(12) United States Patent
Metz-Stavenhagen

(10) Patent No.: US 10,166,111 B2
(45) Date of Patent: Jan. 1, 2019

(54) SPINAL IMPLANTS AND RELATED APPARATUS AND METHODS

(71) Applicant: Peter Metz-Stavenhagen, Bad Wildungen (DE)

(72) Inventor: Peter Metz-Stavenhagen, Bad Wildungen (DE)

( * ) Notice: Subject to any disclaimer, the term of this patent is extended or adjusted under 35 U.S.C. 154(b) by 0 days.

(21) Appl. No.: 13/660,644

(22) Filed: Oct. 25, 2012

(65) Prior Publication Data

US 2013/0053965 A1 Feb. 28, 2013

Related U.S. Application Data

(63) Continuation of application No. PCT/DE2011/000439, filed on Apr. 26, 2011.

(30) Foreign Application Priority Data

Apr. 26, 2010 (DE) .................. 10 2010 018 379

(51) Int. Cl.
*A61F 2/44* (2006.01)
*A61F 2/46* (2006.01)
*A61F 2/30* (2006.01)

(52) U.S. Cl.
CPC .............. *A61F 2/44* (2013.01); *A61F 2/4611* (2013.01); *A61F 2/4465* (2013.01);
(Continued)

(58) Field of Classification Search
CPC ...... A61F 2/4455; A61F 2/4465; A61F 2/447; A61F 2/4611; A61F 2/44;
(Continued)

(56) References Cited

U.S. PATENT DOCUMENTS 5,236,460 A * 8/1993 Barber .................... A61F 2/441
403/109.7
5,290,312 A * 3/1994 Kojimoto et al. ......... 623/17.15
(Continued)

FOREIGN PATENT DOCUMENTS

| CN | 101474103 | 7/2009 |
|---|---|---|
| DE | 202004021288 | 6/2007 |

(Continued)

OTHER PUBLICATIONS

Machine translation of Decription of DE-102010018379, 9 pages.*
(Continued)

*Primary Examiner* — Matthew J Lawson
*Assistant Examiner* — Amy R Sipp
(74) *Attorney, Agent, or Firm* — Hanley, Flight and Zimmerman, LLC

(57) ABSTRACT

Example spinal implants and related apparatus, tools and methods are disclosed. An example spinal implant includes an outer corpus and an inner corpus axially displaceably coupled to the outer corpus. The example implant includes a transport admission provided on at least one of the outer corpus or the inner corpus and a lever admission provided on the other of the inner corpus or the outer corpus. The lever admission and the transport admission are arranged to receive a tool, wherein the tool to distract the spinal implant. The example further includes a tool lock arranged in the transport admission to lock the tool and a lever rotator engagement device provided in the lever admission. The lever rotator engagement device is to engage a lever rotator of the tool. In addition, the example includes a first guide provided on the inner corpus and a second guide provided on the outer corpus. The first guide and the second guide allow an axial displacement of the inner corpus relative to the outer corpus and prevent a rotation of the inner corpus relative to (Continued)

the outer corpus. In addition, in the example, the first guide and the second guide include a tongue and groove.

13 Claims, 8 Drawing Sheets

(52) U.S. Cl.
CPC ............... *A61F 2002/3069* (2013.01); *A61F 2002/30398* (2013.01); *A61F 2002/30426* (2013.01); *A61F 2002/30507* (2013.01); *A61F 2002/30523* (2013.01); *A61F 2002/30601* (2013.01); *A61F 2002/4475* (2013.01); *A61F 2220/0025* (2013.01)

(58) Field of Classification Search
CPC ...... A61F 2002/4627; A61F 2002/4475; A61F 2/46; A61F 2/4603; A61F 2/4637; A61F 2002/4625; A61F 2002/4629; A61F 2002/4638; A61F 2002/4642; B25B 15/004; Y10T 403/7075; Y10T 403/7077; Y10T 403/32475; A61B 17/7074; A61B 17/7076; A61B 17/8875–17/8883
USPC ......... 623/17.11–17.16; 403/376, 377, 109.2
See application file for complete search history.

(56) References Cited

U.S. PATENT DOCUMENTS

| | | | |
|---|---|---|---|
| 5,443,515 A * | 8/1995 | Cohen et al. | 623/17.16 |
| 5,885,299 A * | 3/1999 | Winslow | A61B 17/861 606/247 |
| 6,610,090 B1 * | 8/2003 | Bohm | A61F 2/44 623/17.11 |
| 6,752,832 B2 | 6/2004 | Neumann | |
| 6,902,579 B2 * | 6/2005 | Harms et al. | 623/17.11 |
| 7,029,498 B2 * | 4/2006 | Boehm et al. | 623/17.11 |
| 7,776,091 B2 * | 8/2010 | Mastrorio et al. | 623/17.15 |
| 7,918,891 B1 * | 4/2011 | Curran | A61F 2/447 623/17.16 |
| 8,182,535 B2 | 5/2012 | Kraus | |
| 8,273,126 B2 * | 9/2012 | Lindner | 623/17.15 |
| 8,337,558 B2 * | 12/2012 | Lindner | 623/17.15 |
| 8,357,181 B2 * | 1/2013 | Lange et al. | 606/248 |
| 8,585,763 B2 * | 11/2013 | Olevsky et al. | 623/17.16 |
| 8,685,100 B2 * | 4/2014 | Jodaitis et al. | 623/17.16 |
| 8,690,886 B2 * | 4/2014 | Fedorov et al. | 606/99 |
| 9,788,960 B2 | 10/2017 | Metz-Stavenhagen | |
| 2002/0082695 A1 * | 6/2002 | Neumann | 623/17.11 |
| 2002/0082696 A1 | 6/2002 | Harms et al. | |
| 2003/0163199 A1 * | 8/2003 | Boehm | A61F 2/44 623/17.11 |
| 2006/0004376 A1 * | 1/2006 | Shipp | A61F 2/4611 606/99 |
| 2006/0004447 A1 * | 1/2006 | Mastrorio | A61B 17/7065 623/17.11 |
| 2006/0129238 A1 * | 6/2006 | Paltzer | A61F 2/447 623/17.11 |
| 2006/0195096 A1 * | 8/2006 | Lee | A61B 17/7037 606/278 |
| 2006/0241770 A1 * | 10/2006 | Rhoda et al. | 623/17.15 |
| 2007/0028710 A1 * | 2/2007 | Kraus | A61F 2/44 74/400 |
| 2007/0043378 A1 * | 2/2007 | Kumar | A61B 17/7082 606/104 |
| 2007/0131070 A1 * | 6/2007 | Hull | B25B 13/461 81/489 |
| 2007/0191954 A1 | 8/2007 | Hansell et al. | |
| 2007/0233098 A1 | 10/2007 | Mastrorio et al. | |
| 2008/0243254 A1 * | 10/2008 | Butler | 623/17.16 |
| 2008/0288071 A1 * | 11/2008 | Biyani | A61F 2/44 623/17.11 |
| 2009/0012528 A1 * | 1/2009 | Aschmann | A61B 17/7065 606/99 |
| 2009/0112220 A1 | 4/2009 | Kraus | |
| 2009/0112320 A1 | 4/2009 | Kraus | |
| 2009/0192611 A1 * | 7/2009 | Lindner | 623/17.11 |
| 2009/0192612 A1 * | 7/2009 | Lindner | 623/17.11 |
| 2010/0057204 A1 * | 3/2010 | Kadaba | A61F 2/44 623/17.12 |
| 2010/0100100 A1 * | 4/2010 | Refai et al. | 606/99 |
| 2010/0179594 A1 * | 7/2010 | Theofilos | A61F 2/44 606/247 |
| 2010/0274357 A1 | 10/2010 | Miller et al. | |
| 2010/0298942 A1 | 11/2010 | Hansell et al. | |
| 2011/0178598 A1 | 7/2011 | Rhoda et al. | |
| 2011/0251691 A1 * | 10/2011 | McLaughlin | A61F 2/44 623/17.16 |
| 2012/0179255 A1 | 7/2012 | DeFalco et al. | |
| 2012/0203288 A1 * | 8/2012 | Lange | A61B 17/7082 606/305 |
| 2013/0053965 A1 | 2/2013 | Metz-Stavenhagen | |
| 2013/0282120 A1 | 10/2013 | Refai et al. | |

FOREIGN PATENT DOCUMENTS

| | | |
|---|---|---|
| EP | 1219266 | 7/2002 |
| EP | 2055270 | 5/2009 |
| JP | 2008536649 | 9/2008 |
| WO | 2008121312 | 10/2008 |
| WO | 2009151734 | 12/2009 |
| WO | 2011134457 | 11/2011 |

OTHER PUBLICATIONS

International Searching Authority, "International Preliminary Report on Patentability," issued in connection with application No. PCT/DE2012/000392, dated Oct. 29, 2013, 9 pages.

German Language Report of the International Searching Authority, issued by the International Searching Authority in connection with International Patent Application No. PCT/DE2011/000439, 5 pages.

German Language Office Action, issued by the German Patent and Trademark Office in connection with German Patent Application No. DE 10 2010 019 379.2-35, dated Dec. 21, 2010, 5 pages.

English Translation of Written Opinion of the International Searching Authority, issued by the International Searching Authority in connection with International Patent Application No. PCT/DE2011/000439, 5 pages.

International Searching Authority, "International Search Report," with English translation (pp. 6-8), issued in connection with application No. PCT/DE2012/000392, dated Sep. 4, 2012, 8 pages.

International Searching Authority, "Written Opinion of the International Searching Authority," issued in connection with application No. PCT/DE2012/000392, dated Sep. 4, 2012, 5 pages.

English Translation of International Search Report, issued by the International Searching Authority in connection with International Patent Application No. PCT/DE2011/000439, 3 pages.

Non-Final Office Action, issued by the United States Patent and Trademark Office in connection with U.S. Appl. No. 14/063,989, dated Oct. 20, 2014, 29 pages.

Restriction Requirement, issued by the United States Patent and Trademark Office in connection with U.S. Appl. No. 14/063,989, dated Aug. 15, 2014, 7 pages.

United States Patent Office, Office Action issued in connection with U.S. Appl. No. 14/063,989 dated Aug. 5, 2015, 32 pages. (Copy not provided as this is a USPTO document. Applicant will provide document upon request from Examiner).

United States Patent and Trademark Office, "Non-Final Office Action," issued in connection with U.S. Appl. No. 14/063,989, dated Apr. 7, 2016, 28 pages. (Copy not provided as this is a USPTO document. Applicant will provide document upon request from Examiner.).

English Translation of "International Preliminary Report on Patentability", issued by the International Searching Authority in connection with International Patent Application No. PCT/DE2011/000439, dated Oct. 30, 2012, 6 pages.

(56) References Cited

OTHER PUBLICATIONS

English Translation of "Written Opinion of the International Searching Authority", issued by the International Searching Authority in connection with International Patent Application No. PCT/DE2012/000392, dated Jan. 11, 2012, 8 pages.

English Machine Translation of German Language Office Action issued by the German Patent and Trademark Office in connection with German Patent Application No. DE10 2010 019 379.2-35 dated Dec. 21, 2010, 10 pages.

United States Patent and Trademark Office, "Final Office Action," issued in connection with U.S. Appl. No. 14/063,989, dated May 15, 2017, 38 pages. (Copy not provided as this is a USPTO document. Applicant will provide document upon request from Examiner).

United States Patent and Trademark Office, "Notice of Allowance," issued in connection with U.S. Appl. No. 14/063,989, dated Aug. 11, 2017, 33 pages. (Copy not provided as this is a USPTO document. Applicant will provide document upon request from Examiner).

* cited by examiner

SPINAL IMPLANTS AND RELATED APPARATUS AND METHODS

RELATED APPLICATIONS

This patent arises from a continuation of International Patent Application Serial No. PCT/DE2011/000439, filed Apr. 26, 2011, which claims priority to German Patent Application No. 10 2010 018 379.2, filed on Apr. 26, 2010, both of which are hereby incorporated herein by reference in their entireties.

FIELD OF THE DISCLOSURE

The present disclosure relates generally to medical implants and, more specifically to spinal implants and related apparatus and methods.

BACKGROUND

A distractible spinal implant composed of two U-shaped parts is known from U.S. Pat. No. 7,029,498 B2, in which the two parts are held so that they are axially displaceable against each other in the manner of a telescope. On the free bars of the U-shaped outer part a transport admission is arranged, into which a grasping forceps is insertable. The attending physician can grasp the spinal implant with this grasping forceps and transport it to the desired location.

Once the spinal implant is positioned, the grasping forceps is removed. In order to distract the spinal implant to the desired size, an oblong guide bar is then led through the opening of the U-shaped part into the inside of the spinal implant and screwed into a thread available on the outer part before pushing a hollow toothed instrument over the guide bar. The toothed instrument is thereby pushed into the spinal implant until outer teeth provided on the toothed instrument engage with correspondingly formed teeth on the inner part of the spinal implant. If one now rotates the toothed instrument about its longitudinal axis, the inner part of the spinal implant is displaced relative to the outer part.

This entire process is very difficult and requires a high degree of dexterity on the part of the surgeon. Since the toothed instrument sits only very loosely on the guide bar, it can happen that during distraction it accidentally slips out of the engagement with the teeth, so that it needs to be inserted again.

BRIEF DESCRIPTION OF THE DRAWINGS

FIGS. 1 to 3 show a first example of a spinal implant 10 according to the teachings of this disclosure and an example of a tool 12 according to the teachings of this disclosure.

DETAILED DESCRIPTION

Figure 1:
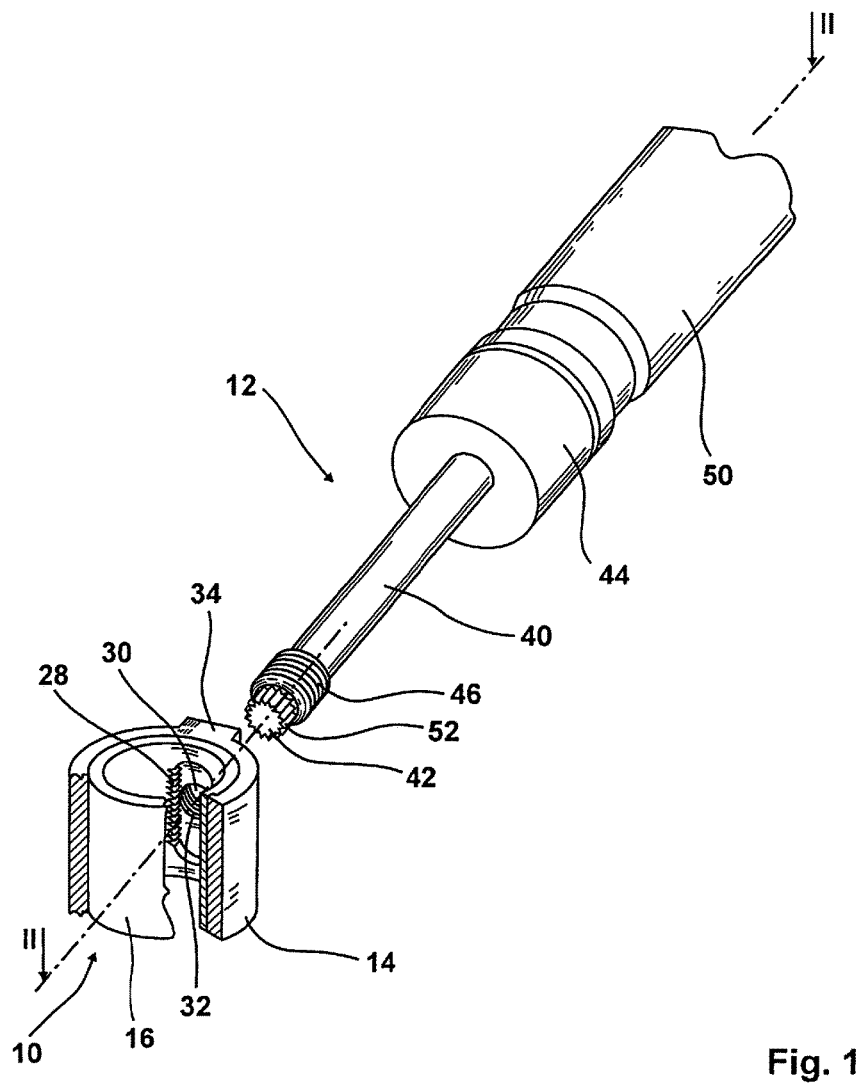
FIG. 1 shows a perspective representation of a first example of a spinal implant according to the teachings of this disclosure and of a tool according to the teachings of this disclosure.

One object of the present disclosure is to develop a spinal implant and a tool for this purpose of increased positionability and stability, so that the spinal implant can be easily and precisely implanted and distracted.

As a technical solution to this objective, example spinal implants and related apparatus and methods of the type claimed are proposed. Advantageous implementations of these example spinal implants, example apparatus and tools and example methods can be gathered from the respective sub-claims.

A spinal implant configured according to this technical teaching has the advantage that the transport as well as the distraction can be carried out with only one tool. This more specifically saves the arduous insertion of the second instrument after placing the implant.

Another advantage of the spinal implant according to the disclosure is that the spinal implant can be reliably held, transported and implanted with one single tool and that the spinal implant can also be positioned and distracted with the same tool, but most notably that the tool can be used with one single hand, so that the other hand is available to the surgeon for other tasks.

In some examples, locking means are formed on the tool and on the implant, with which the tool can be locked on the implant. With a tool locked on the implant in this manner, it is also possible to move the implant in the body with only one hand, in order to position it accurately. Whether the tool is locked on the inner or the outer corpus does not play any role thereby.

In some examples, the locking occurs by way of a rotation lock, an inner thread being configured in the transport admission, while a corresponding outer thread is provided on the transport bar of the tool. With such a rotating lock, the tool can be quickly and easily locked on the implant. Hereby, the tool can also be used for holding the implant. With a tool that is connected to the implant in this manner, the implant can be transported or repositioned with only one hand by the attending physician.

As an alternative to the rotation lock, the locking means can also be configured as a bayonet lock, wherein a bayonet admission is formed in the transport admission, while corresponding bayonet bars are provided on the tool. With such a bayonet lock, the tool can be quickly and easily attached to the implant.

Another alternative example includes in configuring the locking means as a toothed lock, an outer gear ring being formed on the tool, the teeth of which engage with corresponding teeth of the inner gear ring of the transport admission, in order to form a positive-fit.

Yet another advantage is that due to the positive-fit engagement of the tool in the wall teeth, it is also possible to distract the inner corpus, or the outer corpus, with little effort even when it is already implanted and even when it is loaded.

In an example, guiding means are disposed on the inner and on the outer corpus, which prevent the inner corpus from twisting relative to the outer corpus and at the same time ensure an axial guidance. This has the advantage that circumferential forces, which may occur during distraction, do not lead the inner corpus to rotate out of place. It has proven advantageous to configure these guiding means according to the tongue and groove principle. Thereby, a coaxially disposed groove, formed for example in the inner corpus, engages with a protrusion, correspondingly formed on the inner wall of the outer corpus. The guidance of the inner corpus along a certain length of the spinal implant occurs by way of this tongue and groove construction, so that a jamming can be reliably prevented.

Other advantages of the example spinal implants disclosed herein, of the example apparatus and tools disclosed herein, and of the example methods disclosed herein can be gathered from the attached drawings and the examples disclosed in the following. According to the disclosure, the afore-mentioned features as well as the ones that will be further described can be respectively used individually or in any combination. The mentioned examples must not be understood as a conclusive enumeration but as examples.

Turning to the figures, the example spinal implant of FIG. 1 includes an outer corpus 14 and an axially displaceable inner corpus 16 held therein, which in the present example, are both cylindrical. Guiding means 18 are arranged on both corpuses 14, 16, which guide the axial movement of the two corpuses 14, 16 and blocks a rotation of the corpuses 14, 16 relative to each other. The guiding means 18 includes a coaxially oriented groove 20 set in an outer side of the inner corpus 16 and a protrusion 22 formed on an inner side of the outer corpus 14 so that it corresponds to the groove 20.

A lever admission 26 designed as a coaxially oriented long hole is arranged in the inner corpus 16, on the right or left vertical flank of which a number of wall teeth 28 are arranged.

A transport admission 30 designed as an opening, into which is set an inner thread 32, is provided in the outer corpus 14. In the area of the transport admission 30, the outer corpus 14 is reinforced, so that a flange-type shoulder 34 is formed here.

The groove 20, the protrusion 22, the inner corpus 16 and the outer corpus 14 are disposed in such a manner that the lever admission 26 formed as a long hole is aligned with the transport admission 30 designed as an opening, so that a tool 12 can be pushed through the transport admission 30 into the lever admission 26.

The tool 12 is composed of an instrument admission with a transport rod 40 and a lever rotator 42, as well as a handle. The handle is designed in two parts and is composed of a transport handle 44 and a lever handle 50.

The transport rod 40 includes a transport handle 44 arranged at the proximal end and an outer thread 46 arranged at the distal end. The lever rotator 42 includes an oblong shaft 48, on the proximal end of which a lever handle 50 is attached and on the distal end of which a number of circumferential teeth 52 are attached.

The transport rod 40 is hollow on the inside and receives the shaft 48 of the lever rotator 42 in this hollow space. Thereby, the shaft 48 is chosen in such a manner that the circumferential teeth 52 protruding radially at the distal end of the shaft 48 on the one hand and the lever handle 50 on the other hand hold the lever rotator 42 on the transport rod 40 in an accurately and positive fitting manner. This two-part configuration of the tool 12 allows moving the transport rod 40 independently from the lever rotator 42.

Figure 2:
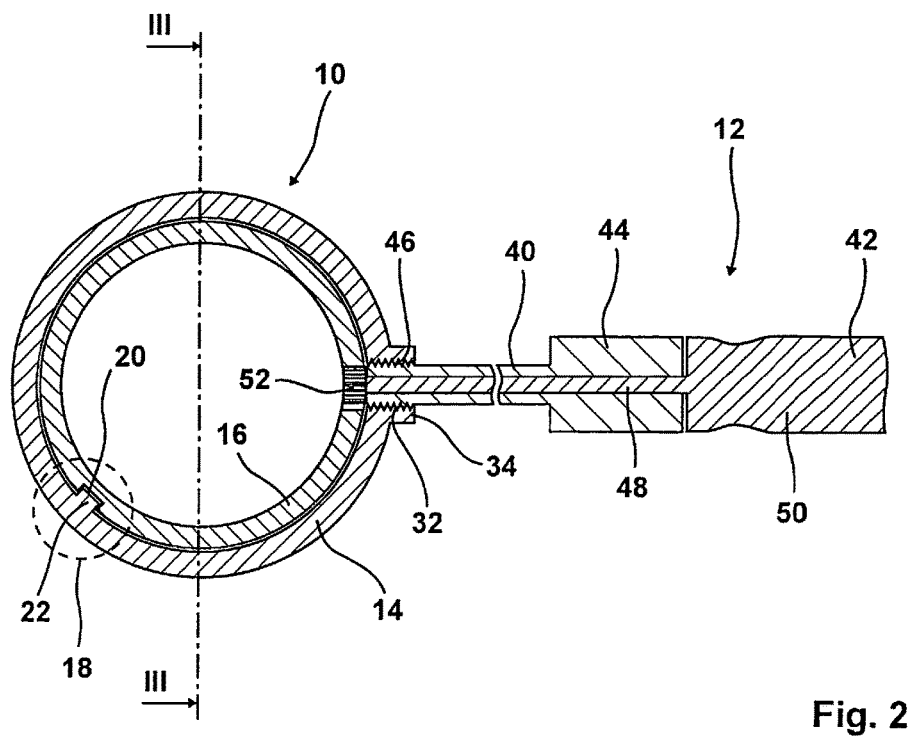
FIG. 2 shows a sectional representation of a view from above onto the spinal implant and the tool according to FIG. 1, cut along the line II-II in FIG. 1.
Figure 3:
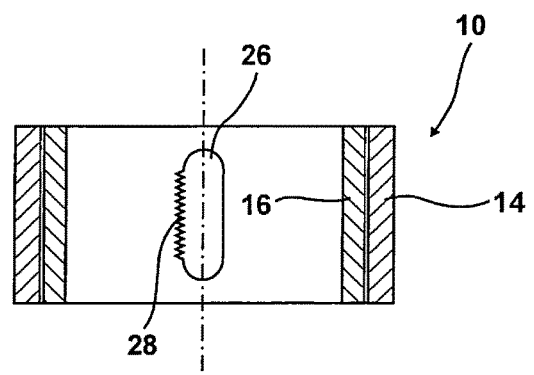
FIG. 3 shows a sectional representation of a lateral view of the spinal implant according to FIG. 1; cut along the line III-III in FIG. 2.

In the example shown in FIGS. 1 to 3, the radially protruding circumferential teeth 52 are distributed along the entire circumference of the shaft 48, so that a complete ring of circumferential teeth 52 is formed. In the first example shown in FIGS. 1 to 3, the tool 12 can be held on the implant by means of a rotation lock. This rotation lock includes the outer thread 46 disposed on the transport rod 40 of the tool 12 as well as the inner thread 32 disposed in the opening of the transport admission 30 of the outer corpus 14, the outer thread 46 and the inner thread 32 matching each other. In the following, the use of the tool 12 on the spinal implant 10 is briefly described:

During a surgical intervention, the attending physician determines the size of the spinal implant 10 to be inserted. The tool 12 can then be attached to the spinal implant 10 with its transport rod 40, for example by an assistant. This occurs by screwing the outer thread 46 located at the distal end of the transport rod 40 into the inner thread 32 on the outer corpus 14. Thereby, a positive-fitting and very stable connection between the tool 12 and the spinal implant 10 is formed.

At a given moment, the attending physician can now hold the tool 12 by the handle, alternatively by the transport handle 44 and/or by the lever handle 50 and thereby not only holds the tool 12 firmly in his hand but also the spinal implant 10 screwed thereon. The attending physician only needs one hand for this and can carry out other activities with the other hand.

The attending physician can now bring the spinal implant 10 held by way of the tool 12 to the desired place in the body of the patient and place it there as desired. Due to the positive-fit connection between the tool 12 and the spinal implant 10, it is possible for the attending physician to exert forces onto the spinal implant 10 with only one hand, in order to place it at the desired place and in the desired form, even under difficult operating conditions.

Once the spinal implant 10 has been implanted, a distraction of the spinal implant 10 can be carried out by the attending physician by holding the lever handle 50 of the lever rotator 42 and rotating it in the desired direction. The circumferential teeth 52 attached to the distal end of the lever rotator 42 thereby engage with the wall teeth 28 on the inner corpus 16 and displace it axially. The inner corpus 16 is prevented from deviating relative to the outer corpus 14 by the guiding means 18, more specifically by the groove 20 and the protrusion 22, so that a precise axial displacement of the inner corpus 16 occurs.

Due to the lever effect of the lever rotator 42, the inner corpus 16 can be correspondingly distracted, even if the spinal implant 10 is already loaded. A jamming of the spinal implant 10 is prevented amongst others by the guiding means 18.

After the spinal implant 10 has been distracted in an appropriate manner, it can be fixed in the desired position by inserting corresponding locking screws. The tool 12 is then screwed out of the outer corpus 14 of the spinal implant 10 by unscrewing the transport rod 40 and can be completely removed.

Should a correction of the spinal implant 10 be required, this can be implemented with the tool 12 in an analog manner.

Figure 4:
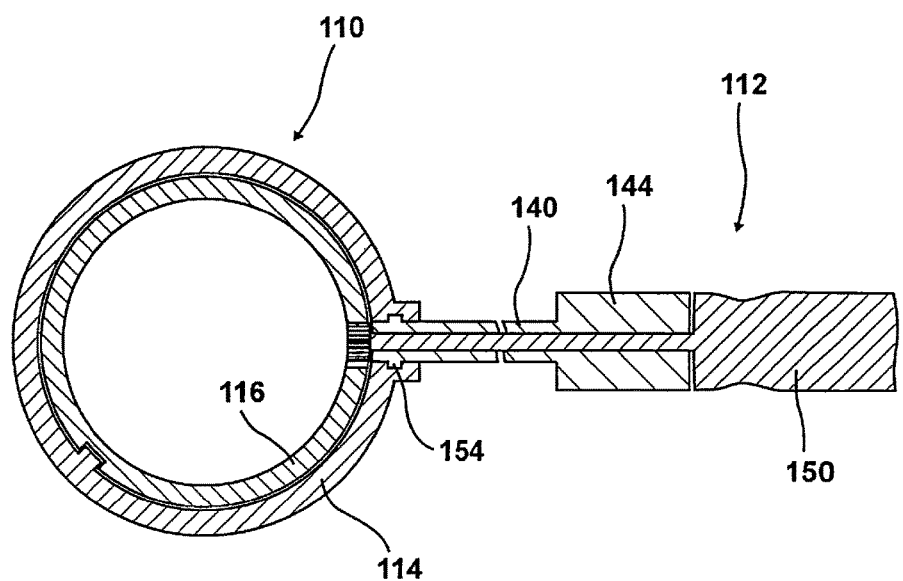
FIG. 4 shows a sectional representation of a view from above onto a second example of a spinal implant according to the teachings of this disclosure and of a tool according to the teachings of this disclosure.
Figure 5:
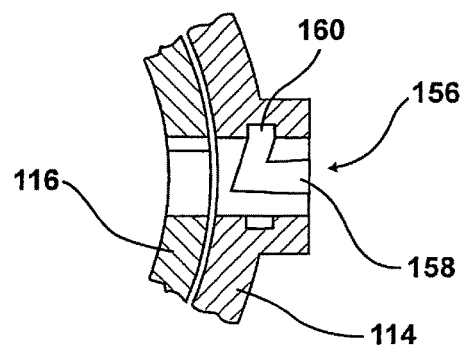
FIG. 5 shows a sectional representation of a view from above onto the spinal implant according to FIG. 4.

The second example shown in FIGS. 4 and 5 includes locking means that are not implemented as a rotation lock but as a bayonet lock. Two bayonet bars 154 protruding radially from the distal end of the transport rod 140 of the tool 112 and corresponding bayonet admissions 156 set in the transport admission 130 of the outer corpus 114 of the spinal implant 110 are part of this bayonet lock. In order to attach the tool 112 to the spinal implant 110, the tool 112 is grasped with one hand at the handle and the free end of the transport rod 140 is introduced with the bayonet bars 154 into the bayonet admissions 156 in the transport admission 130 of the outer corpus 114. The transport rod 140 is then rotated about its longitudinal axis so that the bayonet bars 154 are introduced deeply into the bayonet admissions 156.

As can be more specifically gathered from FIG. 5, the bayonet admission 156 arranged in the outer corpus 114 includes a funnel-shaped tapered entry channel 158, in order to facilitate the insertion of the bayonet bars 154, as well as a locking channel 160, the locking channel 160 being disposed at an acute angle relative to the entry channel 158. The arrangement at an acute angle of, for example, about 80° has the advantage that the inner corpus 116 pressing against the locking rod 140 presses the bayonet bars 154 into the bayonet admission 156 and thus hinders an unintentional loosening of the bayonet lock. Accordingly, in order to remove the tool 112, the bayonet bars 154 must be moved along the diagonally disposed locking channel 160 and thereby push the inner corpus 116 to the side before the bayonet lock can be definitely released.

Figure 6:
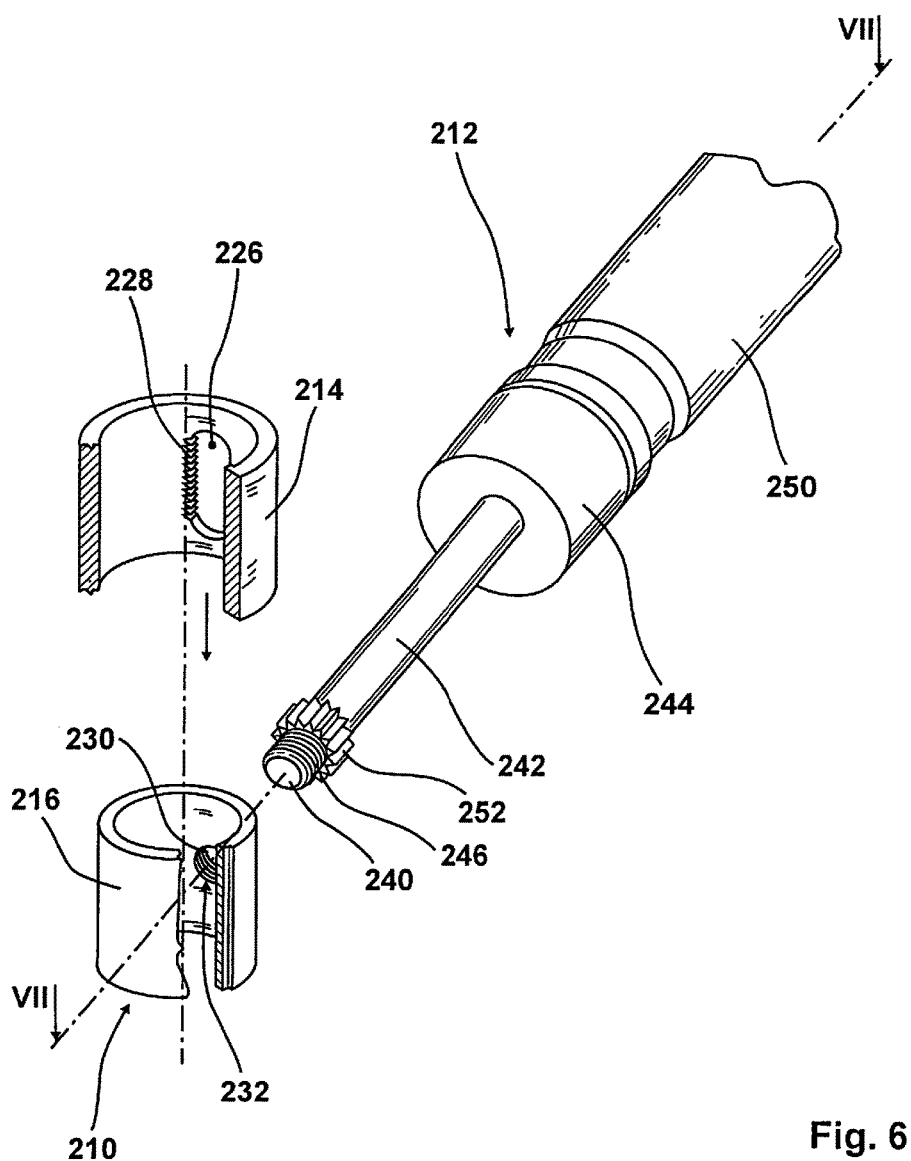
FIG. 6 shows a perspective representation of a third example of a spinal implant according to the teachings of this disclosure and of a tool according to the teachings of this disclosure.
Figure 7:
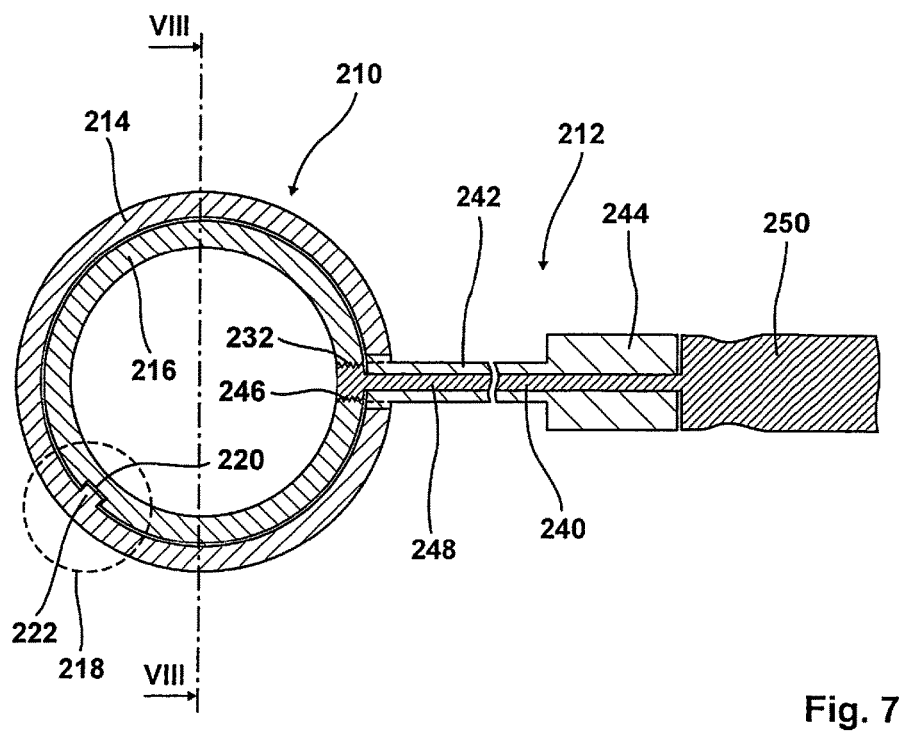
FIG. 7 shows a sectional representation of a view from above onto the spinal implant and the tool according to FIG. 6, cut along the line VII-VII in FIG. 6.
Figure 8:
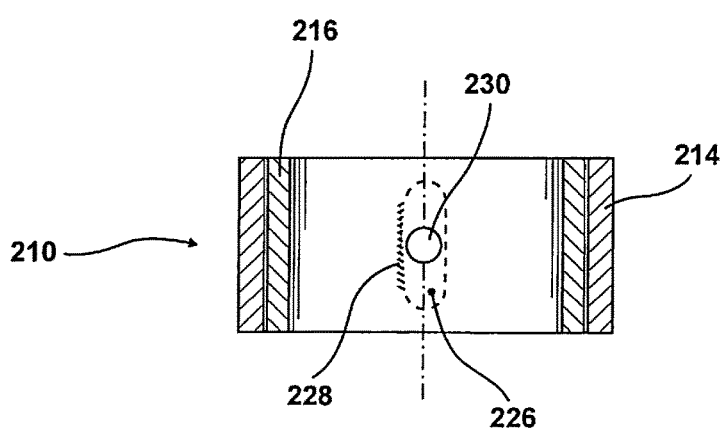
FIG. 8 shows a sectional representation of a lateral view of the spinal implant according to FIG. 6, cut along the line VIII-VIII in FIG. 6.

A third example shown in FIGS. 6 to 8 includes a rotation lock installed on the inner corpus 216 instead of the outer corpus 114. The example of FIGS. 6 to 8 also show a corresponding tool 12.

The spinal implant according to this example includes a cylindrically configured outer corpus 214 and an inner corpus 216 that is also cylindrical, held therein in an axially displaceable manner, a guiding means 218 being formed that guides the two cylinders and blocks a rotation of the cylinders relative to each other. The guiding means 218 includes a coaxially oriented groove 220 set on the outer side of the inner corpus 216 and a protrusion 222 formed on an inner side of the outer corpus 214 so that it corresponds to the groove 220.

A lever admission 226 designed as a coaxially oriented long hole is arranged in the outer corpus 214, on the right or left vertical flank of which a number of wall teeth 228 are arranged. Thereby, the wall teeth are disposed linearly. A transport admission 230, into which is set an inner thread 232, is provided in the inner corpus 216.

The groove 220, the protrusion 222, the inner corpus 216 and the outer corpus 214 are disposed in such a manner that the lever admission 226 is aligned with the transport admission 230, so that a tool 212 can be pushed through lever admission 226 into the transport admission 230.

The tool 212 is composed of an instrument admission with a transport rod 240 and a lever rotator 242, as well as a handle. The handle is designed in two parts and is composed of a transport handle 244 and a lever handle 250.

The transport rod 240 includes an oblong shaft 248, at the proximal end of which a transport handle 244 is attached and at the distal end of which an outer thread 246 is attached. The lever rotator 242 includes a lever handle 250, formed at the proximal end, and at the distal end, a number of circumferential teeth 252. The lever rotator 242 is hollow on the inside and receives the shaft 248 of the transport rod 240 in this hollow space. Thereby, the shaft 248 is chosen in such a manner that the outer thread 246 disposed at the distal end of the shaft 248 on the one hand, and the lever handle 250 on the other hand, hold the lever rotator 242 with its radially protruding circumferential teeth 252 on the transport rod 240 in an accurately fitting manner. This two-part configuration of the tool 212 allows moving the transport rod 240 independently from the lever rotator 242.

In the example shown in FIGS. 6 to 8, the radially protruding circumferential teeth 252 are distributed along the entire circumference of the lever rotator 242, so that a complete ring of circumferential teeth 252 is formed. Thereby, the tool 212 can be held on the implant by means of a rotation lock. This rotation lock includes the outer thread 246 installed on the transport rod 240 of the tool 212 as well as the inner thread 232 disposed in the transport admission 230 of the inner corpus 216, the outer thread 246 and the inner thread 232 matching each other.

In the following, the use of the tool 212 on the spinal implant 210 is briefly described:

During a surgical intervention, the attending physician determines the size of the spinal implant 210 to be inserted. The tool 212 can then be attached to the spinal implant 210 with its transport rod 240, for example by an assistant. This occurs by screwing the outer thread 246 located at the distal end of the transport rod 240 into the inner thread 232 on the inner corpus 216. Thereby, a positive-fitting and very stable connection between the tool 212 and the spinal implant 210 is formed.

At a given moment, the attending physician can now hold the tool 212 by the handle and thereby not only holds the tool 212 firmly in his hand but also the spinal implant 210 screwed thereon. The attending physician only needs one hand for this and can carry out other activities with the other hand.

The attending physician can now bring the spinal implant 210 held by way of the tool 212 to the desired place in the body of the patient and place it there as desired. Due to the positive-fit connection between the tool 212 and the spinal implant 210, it is possible for the attending physician to exert forces onto the spinal implant 210 with only one hand, in order to place it at the desired place and in the desired form, even under difficult operating conditions.

Once the spinal implant 210 has been implanted, a distraction of the spinal implant 210 can be carried out by the attending physician by holding the lever handle 250 of the lever rotator 242 and rotating it in the desired direction. The circumferential teeth 252 attached to the distal end of the lever rotator 242 thereby engage with the wall teeth 228 on the outer corpus 214 and displace it axially. The inner corpus 216 is prevented from deviating relative to the outer corpus 214 by the guiding means 218, more specifically by the groove 220 and the protrusion 222, so that a precise axial displacement of the outer corpus 214 occurs.

Due to the lever effect of the lever rotator 242, the outer corpus 214 can be correspondingly distracted, even if the spinal implant 210 is already loaded. A jamming of the spinal implant 210 is prevented amongst others by the guiding means 218.

Once the spinal implant 210 has been distracted in an appropriate manner, it can be fixed in the desired position by inserting corresponding locking screws. The tool 212 is then screwed out of the inner corpus 216 of the spinal implant 210 by unscrewing the transport rod 240 and can be completely removed.

Should a correction of the spinal implant 210 be required, this can be implemented with the tool 212 in an analog manner.

Figure 9:
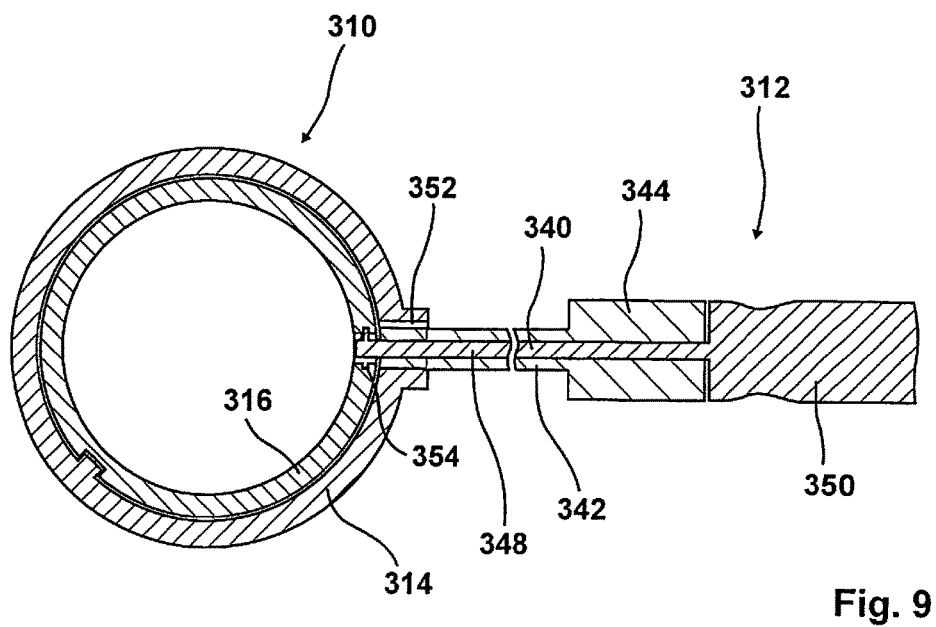
FIG. 9 shows a sectional representation of a view from above onto a fourth example of a spinal implant according to the teachings of this disclosure and of a tool according to the teachings of this disclosure.
Figure 10:
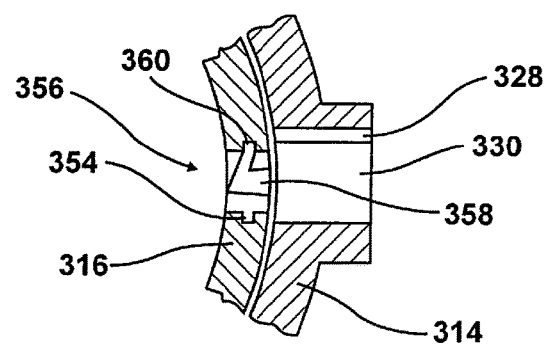
FIG. 10 shows a sectional representation of a view from above of the spinal implant according to FIG. 9.

The fourth example shown in FIGS. 9 and 10 includes a locking device that is not designed as a threaded rotation lock but as a bayonet lock. Two bayonet bars 354 protruding radially from the distal end of the transport rod 340 of the tool 312 and corresponding bayonet admissions 356 set in the transport admission 330 of the inner corpus 316 of the spinal implant 310 are part of this bayonet lock. In order to attach the tool 312 to the spinal implant 310, the tool 312 is grasped with one hand at the handle and the free end of the transport rod 340 is introduced with the bayonet bars 354 into the bayonet admissions 356 in the transport admission 330 of the inner corpus 316. The transport rod 340 is then rotated so that the bayonet bars 354 are introduced deeply into the bayonet admissions 356.

As can be more specifically gathered from FIG. 10, the bayonet admission 356 arranged in the inner corpus 316 includes a funnel-shaped tapered entry channel 358, in order to facilitate the insertion of the bayonet bars 354, as well as a locking channel 360, the locking channel 360 being disposed at an acute angle relative to the entry channel 358. The arrangement at an acute angle of, for example, about 80° has the advantage that the outer corpus 314 pressing against the transport rod 340 presses the bayonet bars 354 into the bayonet admission 356 and thus hinders an unintentional loosening of the bayonet lock. Accordingly, in order to remove the tool 312, the bayonet bars 354 must be moved along the diagonally disposed locking channel 360 and thereby push the outer corpus 316 to the side before the bayonet lock can be definitely released.

Figure 11:
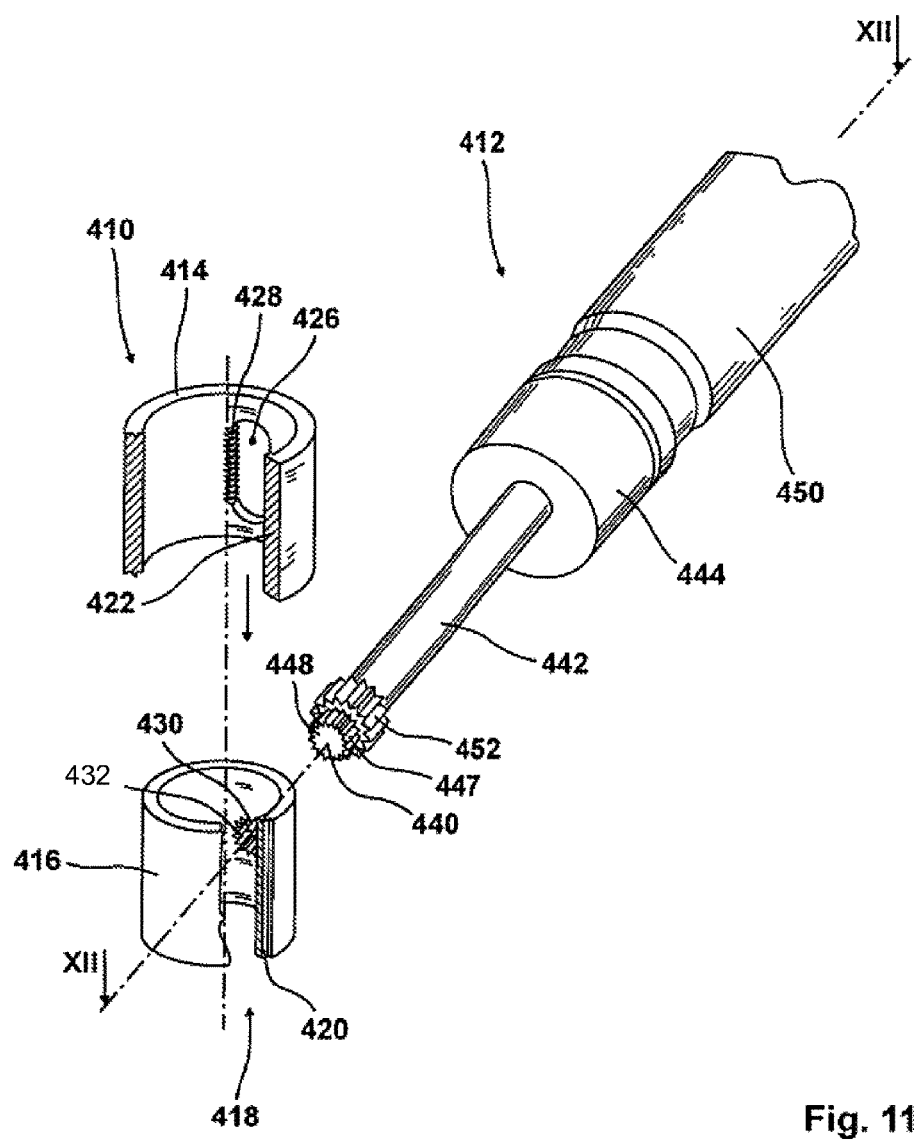
FIG. 11 shows a perspective representation of a fifth example of a spinal implant according to the teachings of this disclosure and of the tool according to the teachings of this disclosure.
Figure 12:
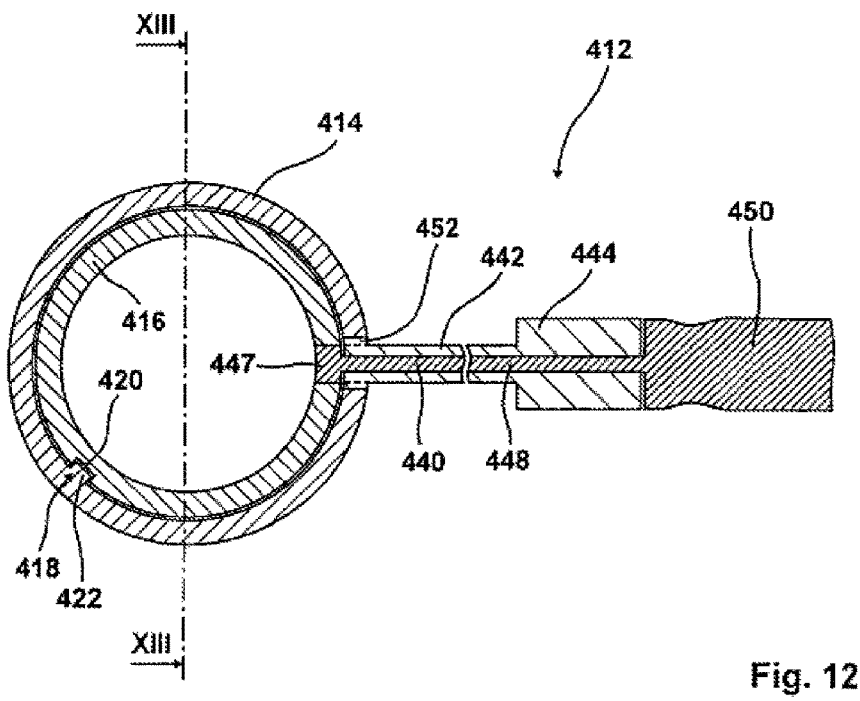
FIG. 12 shows a sectional representation of a view from above onto the spinal implant and the tool according to FIG. 11, cut along the line XII-XII in FIG. 11.
Figure 13:
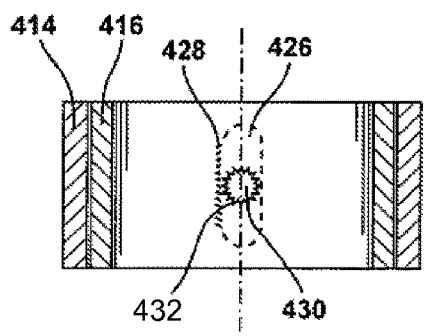
FIG. 13 shows a sectional representation of a lateral view of the spinal implant according to FIG. 11, cut along the line XIII-XIII in FIG. 11.

In FIGS. 11 to 13, another example of a spinal implant 410 according to the teachings of this disclosure and of a apparatus or tool 412 according to the teachings of this disclosure are shown. The spinal implant includes an outer corpus 414 and an inner corpus 416 held therein in an axially displaceable manner, wherein guiding means 418 are arranged, which guide the axial movement of the two corpuses 414, 416 and blocks a rotation of the corpuses relative to each other. The guiding means 418 include a coaxially oriented groove 420 set in an outer side of the inner corpus 416 and a protrusion 422 formed on an inner side of the outer corpus 414 so that it corresponds to the groove 420.

A lever admission 426 designed as a long hole is arranged in the outer corpus 414, on the right or left vertical flank of which a number of wall teeth 428 are arranged. A transport admission 430, into which is set an inner gear ring 432, is provided in the inner corpus 416.

The groove 420, the protrusion 422, the inner corpus 416 and the outer corpus 414 are disposed in such a manner that the lever admission 426 is aligned with the transport admission 430, so that a tool 412 can be pushed through lever admission 426 into the transport admission 430.

The tool 412 is composed of an instrument admission with a transport rod 440 and a lever rotator 442, as well as a handle. The handle is designed in two parts and is composed of a transport handle 444 and a lever handle 450.

The transport rod 440 includes an oblong shaft 448, at the proximal end of which a transport handle 444 is attached, and at the distal end of which an outer gear ring 447 is attached. The lever rotator 442 includes a lever handle 450, formed at the proximal end, and at the distal end, a number of circumferential teeth 452. The lever rotator 442 is hollow on the inside and receives the shaft 448 of the transport rod 440 in this hollow space. Thereby, the shaft 448 is chosen in such a manner that the outer gear ring 447 disposed at the distal end of the shaft 448 on the one hand, and the lever handle 450 on the other hand, hold the lever rotator 442 with its radially protruding circumferential teeth 452 on the transport rod 440 in an accurately fitting manner. This two-part configuration of the tool 412 allows moving the transport rod 440 independently from the lever rotator 442.

In the example shown in FIGS. 11 to 13, the radially protruding circumferential teeth 452 are distributed along the entire circumference of the lever rotator 442, so that a complete ring of circumferential teeth 452 is formed. Thereby, the tool 412 can be held on the implant by means of a toothed lock. This toothed lock includes the outer gear ring 447 installed on the transport rod 440 of the tool 412 as well as the inner gear ring 432 disposed in the transport admission 430 of the inner corpus 416, the outer gear ring 446 and the inner gear ring 432 matching each other.

In the following, the use of the tool 412 on the spinal implant 410 is briefly described:

During a surgical intervention, the attending physician determines the size of the spinal implant 410 to be inserted. The tool 412 can then be attached to the spinal implant 410 with its locking rod 440, for example by an assistant. This occurs by pushing the outer gear ring 247 located at the distal end of the transport rod 440 into the inner gear ring 432 on the inner corpus 416. Thereby, a positive-fitting and very stable connection between the tool 412 and the spinal implant 410 is formed.

At a given moment, the attending physician can now hold the tool 412 by the handle 444, and/or by the handle 450 and thereby not only holds the tool 412 firmly in his hand but also the spinal implant 410 screwed thereon. The attending physician only needs one hand for this and can carry out other activities with the other hand.

The attending physician can now bring the spinal implant 410 held by way of the tool 412 to the desired place in the body of the patient and place it there as desired. Due to the positive-fit connection between the tool 412 and the spinal implant 410, it is possible for the attending physician to exert forces onto the spinal implant 410 with only one hand, in order to place it at the desired place and in the desired form, even under difficult operating conditions.

Once the spinal implant 410 has been implanted, a distraction of the spinal implant 410 can be carried out by the attending physician by holding the lever handle 450 of the lever rotator 442 and rotating it in the desired direction. The circumferential teeth 452 attached to the distal end of the lever 442 thereby engage with the wall teeth 428 on the outer corpus 414 and displace it axially. The inner corpus 416 is prevented from deviating relative to the outer corpus 414 by the guiding means 418, more specifically by the groove 420 and the protrusion 422, so that a precise axial displacement of the outer corpus 414 occurs.

Due to the lever effect of the lever rotator 442, the outer corpus 414 can be correspondingly distracted, even if the spinal implant 410 is already loaded. A jamming of the spinal implant 410 is prevented amongst others by the guiding means 418.

After the spinal implant 410 has been distracted in an appropriate manner, it can be fixed in the desired position by inserting corresponding locking screws. The tool 412 is then screwed out of the inner corpus 416 of the spinal implant 410 by unscrewing the transport rod 440 and can be completely removed.

Should a correction of the spinal implant 410 be required, this can be implemented with the tool 412 in an analog manner.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A spinal implant comprising:
   an outer corpus including a top-most surface, a bottom surface opposite the top surface, and a sidewall extending between the top surface and the bottom surface;
   an inner corpus axially displaceably coupled to the outer corpus along a central axis extending through the inner corpus and the outer corpus, each of the inner corpus and the outer corpus having a cylindrical shape;
   a transport admission provided on the sidewall of the outer corpus, the transport admission including an engagement structure, the transport admission having a first lateral length along an axis perpendicular to the central axis extending through the inner corpus and the outer corpus;
   a lever admission provided on the inner corpus, the lever admission having a second lateral length along the axis perpendicular to the central axis, the second lateral length smaller than the first lateral length, the lever admission and the transport admission aligned about the central axis extending through the inner corpus and the outer corpus and arranged to receive a tool, the tool to distract the spinal implant, the lever admission including a set of teeth, the outer corpus including a flange, the flange including a portion of the engagement structure, a remainder of the engagement structure disposed between the inner corpus and the flange, the flange extending along the sidewall from the top surface to the transport admission; and
   an alignment guide provided on the inner corpus and the outer corpus, the alignment guide including a tongue provided on the outer corpus and a groove provided on the inner corpus, the tongue and groove to allow an axial displacement of the inner corpus relative to the outer corpus and to prevent a rotation of the inner corpus relative to the outer corpus.

2. The spinal implant according to claim 1, wherein the engagement structure includes an inner thread.

3. The spinal implant according to claim 1, wherein the lever admission comprises an elongated aperture and the set of teeth include a plurality of wall teeth formed on a longitudinal side of the lever admission and protruding into the lever admission.

4. The spinal implant according to claim 3, wherein the wall teeth are disposed linearly.

5. A tool for the spinal implant of claim 1, the tool comprising:
   a transport handle;
   a lever handle;
   a spinal implant distractor comprising:
      an oblong lever rotator;
      the lever handle arranged at a first end of the lever rotator; and
      a plurality of circumferential teeth distributed along a second end of the lever rotator, the second end of the lever rotator having a first circumference; and
   a spinal implant transporter, the transporter separably operable from the distractor, and the transporter comprising:
      a transport rod having a hollow shaft, the lever rotator disposed inside the shaft;
      the transport handle coupled to a first end of the transport rod; and
      an implant engagement device coupled to a second end of the transport rod, the second end of the transport rod having a second circumference, the second circumference greater than the first circumference.

6. The tool according to claim 5, wherein the implant engagement device comprises an outer thread.

7. The tool according to claim 5, wherein the implant engagement device and the circumferential teeth are disposed so the circumferential teeth engage with the set of teeth of the lever admission of the spinal implant when the implant engagement device is engaged with the transport admission of the spinal implant.

8. The tool according to claim 5, wherein the spinal implant distractor is to remain coupled to the spinal implant transporter during operation of the spinal implant transporter via the shaft.

9. The tool according to claim 5, wherein the lever handle is distal to the plurality of circumferential teeth of the lever rotator.

10. The tool according to claim 9, wherein during operation of the tool, the circumferential teeth of the second end of the lever rotator engage the implant prior to the implant engagement device of the spinal implant transporter.

11. The tool according to claim 5, wherein the circumferential teeth extend through the transport admission prior to engagement with the set of teeth of the lever admission.

12. The spinal implant according to claim 1, wherein the tongue and the groove extend parallel to the central axis.

13. An apparatus comprising:
   a first corpus including a top-most surface, a bottom surface opposite the top surface, and a sidewall extending between the top surface and the bottom surface;
   a second corpus slidably disposed in the first corpus along a central longitudinal axis extending through the first corpus and the second corpus;
   a transport admission defined in the sidewall of the first corpus, the transport admission including an engagement structure, the transport admission having a first lateral length along an axis perpendicular to the central longitudinal axis extending through the first corpus and the second corpus;
   a lever admission defined in the second corpus, the lever admission having a second lateral length along the axis perpendicular to the central longitudinal axis, the second lateral length smaller than the first lateral length, the lever admission including a set of teeth, the first corpus including a flange, the flange including a portion of the engagement structure, a remainder of the engagement structure disposed between the second corpus and flange, the flange extending along the sidewall from the top surface to the transport admission, the transport admission aligned with the lever admission, the lever admission and the transport admission to receive a tool, the second corpus to slide relative to the first corpus along the central longitudinal axis extending through the first corpus and the second corpus when the tool is disposed in the lever admission and the transport admission;
a tongue formed in a first surface of the first corpus; and
a groove formed in a second surface of the second corpus, the tongue slidable relative to the groove along the central longitudinal axis when the second corpus slides relative to the first corpus.

* * * * *